United States Patent
Hauville

(10) Patent No.: US 6,851,769 B2
(45) Date of Patent: Feb. 8, 2005

(54) MOBILE ISOLATION GLOVE BOX WITH DISPOSABLE ENCLOSURE FOR INVESTIGATIONS

(76) Inventor: Francois P. Hauville, 34 Alcott Way, North Andover, MA (US) 01845

( * ) Notice: Subject to any disclaimer, the term of this patent is extended or adjusted under 35 U.S.C. 154(b) by 0 days.

(21) Appl. No.: 10/280,601

(22) Filed: Oct. 25, 2002

(65) Prior Publication Data

US 2003/0137225 A1 Jul. 24, 2003

Related U.S. Application Data

(60) Provisional application No. 60/350,486, filed on Oct. 25, 2001, and provisional application No. 60/344,907, filed on Nov. 7, 2001.

(51) Int. Cl.[7] .............................................. A61G 11/00
(52) U.S. Cl. ......................................................... 312/1
(58) Field of Search ............................ 312/1; 135/156, 135/115, 116, 119; 600/21

(56) References Cited

U.S. PATENT DOCUMENTS

| | | | | |
|---|---|---|---|---|
| 2,786,740 A | * | 3/1957 | Taylor et al. | 312/1 |
| 3,415,582 A | * | 12/1968 | Trexler | 312/1 |
| 3,596,636 A | * | 8/1971 | Stobaugh | 119/174 |
| 3,875,927 A | * | 4/1975 | Trexler | 600/21 |
| 5,342,121 A | * | 8/1994 | Koria | 312/1 |
| 5,441,708 A | * | 8/1995 | Diccianni et al. | 312/1 |
| 5,685,771 A | * | 11/1997 | Kleppen | 454/56 |
| 6,106,403 A | * | 8/2000 | Zemel | 472/126 |

* cited by examiner

Primary Examiner—Janet M. Wilkens
(74) Attorney, Agent, or Firm—Pandiscio & Pandiscio

(57) ABSTRACT

A mobile, disposable isolation glove box comprising: an enclosure comprising a base and a plurality of inclined walls converging to an apex, at least one of the walls being at least in part transparent; at least one glove formed in at least one of the inclined walls, the at least one glove extending into the interior of the enclosure; and a sealable opening formed in the enclosure for permitting a specimen to be placed inside the enclosure.

30 Claims, 15 Drawing Sheets

MOBILE ISOLATION GLOVE BOX WITH DISPOSABLE ENCLOSURE FOR INVESTIGATIONS

REFERENCE TO PENDING PRIOR PATENT APPLICATIONS

This invention:

(1) claims benefit of pending prior U.S. Provisional Patent Application Ser. No. 60/350,486, filed Oct. 25, 2001 by Francois P. Hauville for MOBILE ISOLATION GLOVE BOX WITH DISPOSABLE ENCLOSURE FOR INVESTIGATIONS; and (2) claims benefit of pending prior U.S. Provisional Patent Application Ser. No. 60/344,907, filed Nov. 7, 2001 by Francois P. Hauville for MOBILE ISOLATION GLOVE BOX WITH DISPOSABLE ENCLOSURE FOR INVESTIGATIONS.

The two above-identified patent applications are hereby incorporated herein by reference.

FIELD OF THE INVENTION

This invention relates to safety enclosures in general, and more particularly to isolation glove boxes for use in handling pathogenic or contaminable substances.

BACKGROUND OF THE INVENTION

It is well known that, in order to handle highly pathogenic substances, all work must generally be conducted within safety enclosures so as to confine the pathogenic substances to a sealed area, thereby ensuring the safety of the handlers.

Such safety enclosures commonly comprise isolation glove boxes. Isolation glove boxes generally comprise an enclosure formed out of an impermeable membrane and configured to permit pathogenic substances to be introduced into, and/or removed from, the enclosure. Gloves are formed in a side wall of the enclosure to permit the user to safely manipulate objects contained within the enclosure.

Isolation glove boxes must generally be decontaminated after each use. This is generally done using complex decontamination systems which add significantly to the size, complexity and cost of the isolation glove boxes. Furthermore, such decontamination is generally time-consuming, thus imposing substantial delays between successive uses of a given isolation glove box.

Thus it will be appreciated that isolation glove boxes are typically large, complex and expensive, and generally require time-consuming decontamination between successive uses. Furthermore, such isolation glove boxes must generally be used by qualified personnel. In essence, isolation glove boxes are generally used by specialists working in research or analytical laboratories in the course of conducting substantial and costly investigations.

However, in some circumstances it may only be necessary to carry out a single, relatively simple and inexpensive investigation. In this situation, the use of a traditional isolation glove box can be quite inefficient, requiring the availability of an expensive isolation glove box for the investigation itself, and thereafter tying up that same isolation glove box for a substantial period of time while its contents are purged and its interior decontaminated. Thus, it would be advantageous to have a relatively simple, inexpensive and disposable isolation glove box available for use in simple and inexpensive investigations.

Furthermore, in many situations it would be advantageous to have a lightweight, mobile isolation glove box which can be used initially at a site in the field, and thereafter be transported, in a sealed condition, to a laboratory for completion of the investigation. For example, disease control specialists might wish to collect a sample at a field site, conduct a limited (but safe) initial investigation at the field site, and then transport the sample in a sealed condition to a laboratory for further investigation. By way of further example, where suspicious packages (e.g., possible anthrax packages) are detected by postal authorities or private courier services, it can be desirable to initially examine the suspicious package in the field, within the safety of an isolation glove box, and then, where appropriate, safely transport the suspicious package to a laboratory for further investigation. And by way of still further example, police investigators might wish to initially examine potential evidence at a crime scene, without fear of contaminating the evidence, and then transport that evidence, in an isolated state, to a laboratory for further analysis. Thus it would be advantageous to have available a lightweight, mobile isolation glove box which can be used initially at a site in the field, and thereafter be transported, in a sealed condition, to a laboratory for completion of the investigation.

SUMMARY OF THE INVENTION

Accordingly, one object of the present invention is to provide a relatively simple, inexpensive and disposable isolation glove box which can be used in simple and inexpensive investigations and thereafter disposed of.

Another object of the present invention is to provide an isolation glove box which is lightweight and mobile, and that is capable being deployed at a field site for initial investigation of a specimen, and then, where necessary, safely transported to another location in a sealed condition for completion of the investigation.

These and other objects are addressed by the present invention, which comprises the provision and use of a novel mobile, disposable isolation glove box.

In one form of the present invention, there is provided a mobile, disposable isolation glove box comprising: an enclosure comprising a base and a plurality of inclined walls converging to an apex, at least one of the walls being at least in part transparent; at least one glove formed in at least one of the inclined walls, the at least one glove extending into the interior of the enclosure; and a sealable opening formed in the enclosure for permitting a specimen to be placed inside the enclosure.

In another form of the present invention, there is provided a mobile, disposable isolation glove box assembly comprising: a mobile, disposable isolation glove box comprising: an enclosure comprising a base and a plurality of inclined walls converging to an apex, at least one of the walls being at least in part transparent; at least one glove formed in at least one of the inclined walls, the at least one glove extending into the interior of the enclosure; and a sealable opening formed in the enclosure for permitting a specimen to be placed inside the enclosure; and a support for supporting the isolation glove box on a worksurface, the support comprising at least one upstanding element extending above the height of the apex and including apparatus for connection to the apex, whereby to support the enclosure in an upright position.

In another form of the present invention, there is provided a method for conducting an investigation of a potentially pathogenic or contaminable specimen, wherein the specimen is located at a first location, the method comprising the steps of: providing a mobile, disposable isolation glove box comprising: an enclosure comprising a base and a plurality of inclined walls converging to an apex, at least one of the walls being at least in part transparent; at least one glove formed in at least one of the inclined walls, the at least one glove extending into the interior of the enclosure; and a sealable opening formed in the enclosure for permitting a specimen to be placed inside the enclosure; placing the specimen inside the enclosure and closing the sealable opening; conducting a preliminary examination using the isolation glove box at the first location; transporting the isolation glove box, with the specimen sealed therein, to a second location; and conducting a follow-up examination using the isolation glove box at the second location.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DESCRIPTION OF THE PREFERRED EMBODIMENTS

Figure 1:
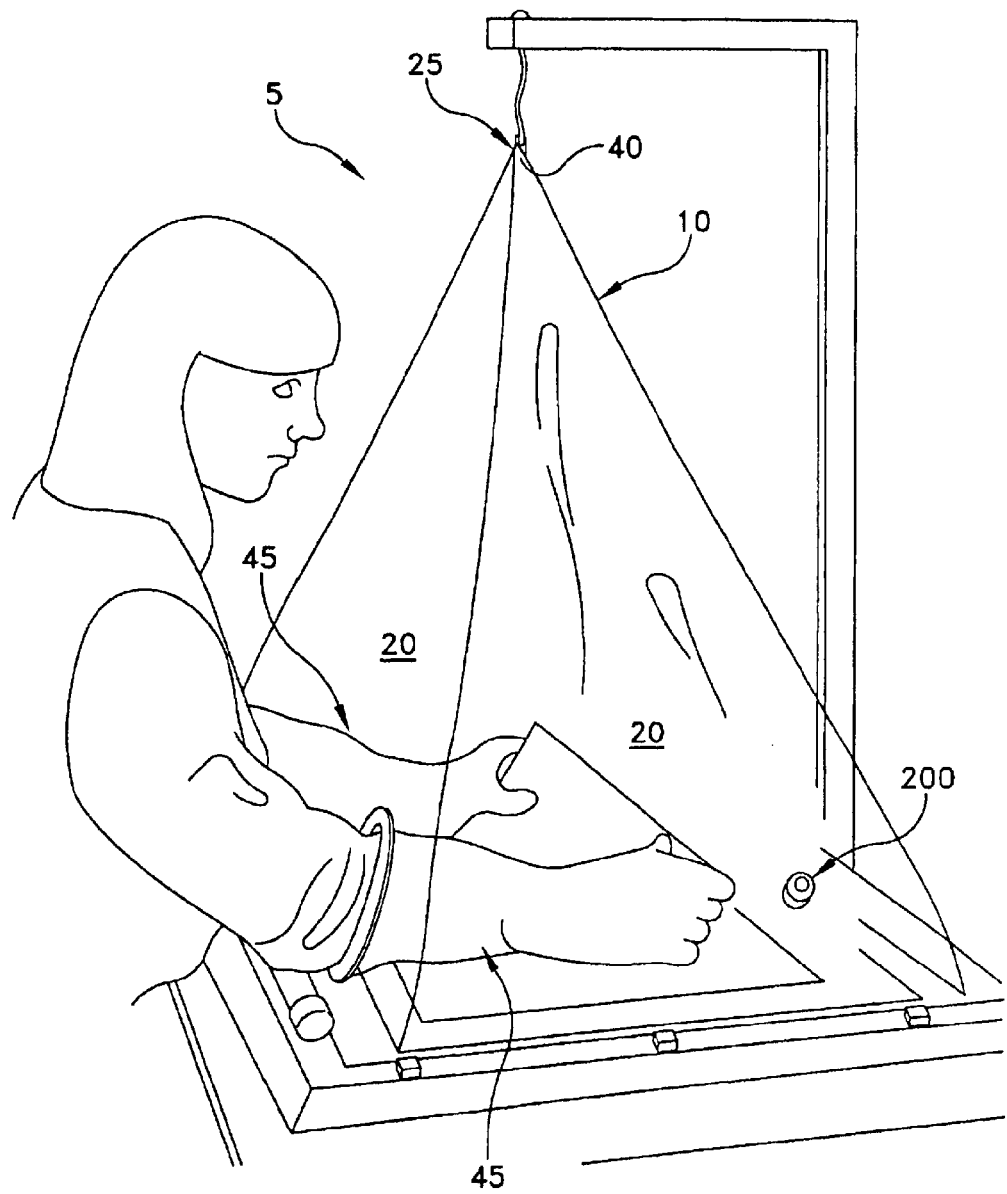
FIG. 1 is a schematic perspective view illustrating a mobile, disposable isolation glove box formed in accordance with the present invention.
Figure 2:
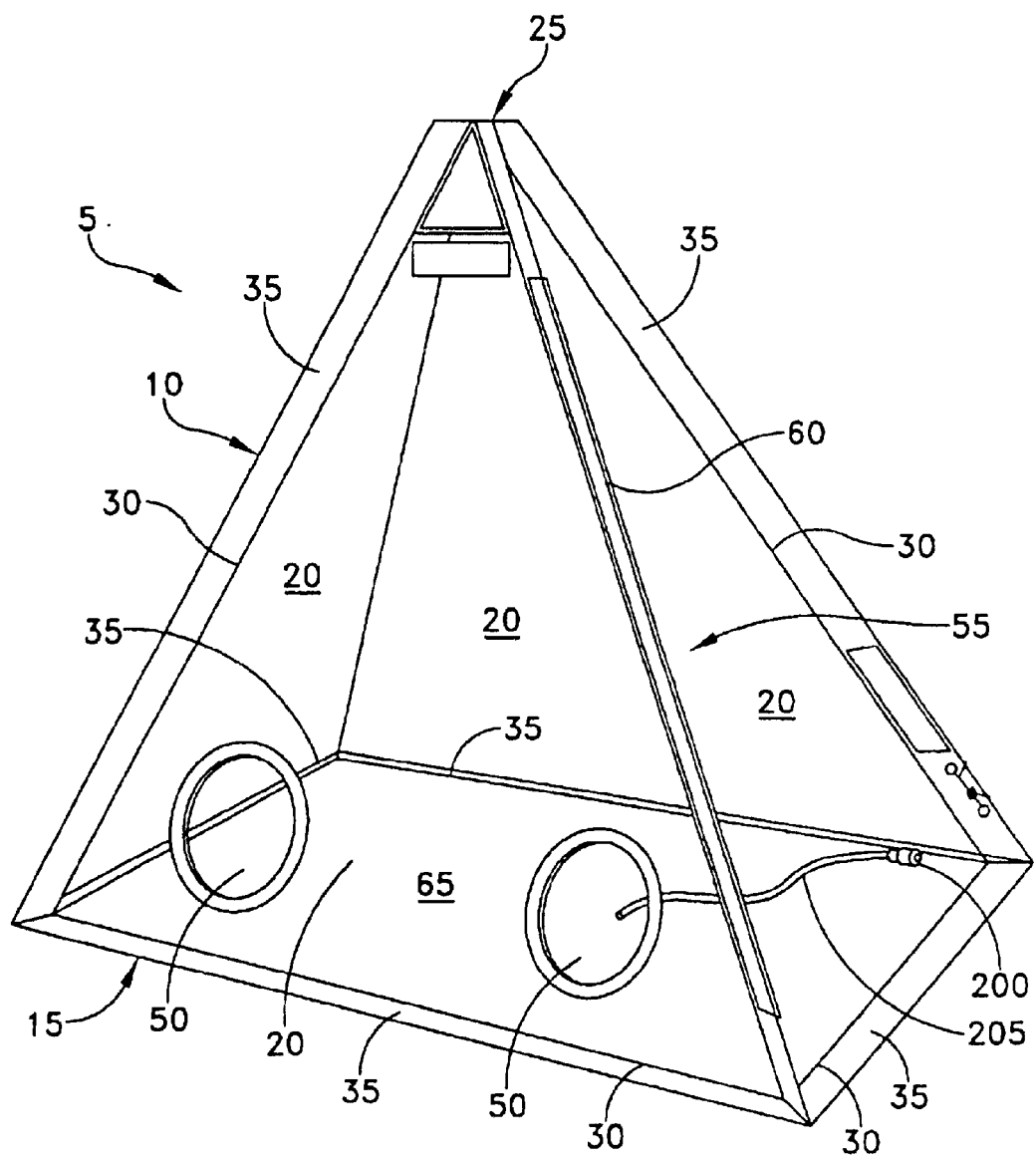
FIG. 2 is a schematic perspective view of the enclosure of the isolation glove box of FIG. 1.

Looking first at FIGS. 1 and 2, there is shown a novel mobile, disposable isolation glove box 5 formed in accordance with the present invention. Isolation glove box 5 comprises a generally pyramidal enclosure 10 formed by a flat base 15 and a plurality of inclined walls 20 converging toward one another at their upper ends. Preferably enclosure 10 comprises a base 15 having four sides (e.g., rectangular or square) and four inclined walls 20 intersecting at an apex 25.

Figure 3:
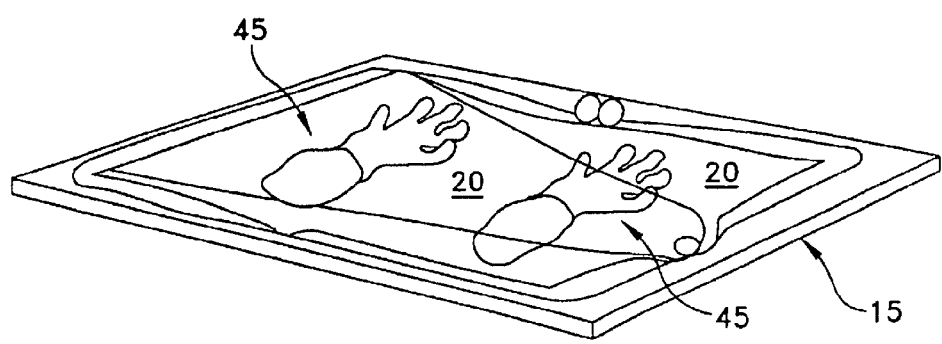
FIG. 3 is a schematic perspective view of the isolation glove box of FIG. 1, with the isolation glove box being shown in a collapsed state.

Base 15 and inclined walls 20 together form a pathogen-impervious enclosure. Base 15 and inclined walls 20 are formed from a suitable transparent, flexible material (e.g., polyvinlychloride, or "PCV") whereby, when fastened together, they form a transparent enclosure which is both (i) self-standing (FIG. 2), and (ii) capable of being folded flat (FIG. 3) if desired, e.g., for storage and/or shipping purposes. Preferably base 15 and inclined walls 20 are fastened together by welding or glueing, e.g., as shown at 30 so as to form the pyramidal enclosure 10. Preferably base 15 and inclined walls 20 are attached so as to leave wings 35 outside the enclosure. Wings 35 have an eyelet 40 formed therein at the apex 25 of the enclosure 10. Eyelet 40 may be used to attach enclosure 10 to a support (see below), preferably with the help of a resilient hook arrangement (see below).

Isolation glove box 5 comprises two or more gloves 45 extending inwardly from one of its inclined walls, thereby allowing for the safe handling of objects located inside enclosure 10. Gloves 45 may be fused or glued to their associated inclined wall 20 at the perimeter of holes 50 formed in that wall.

Figure 4:
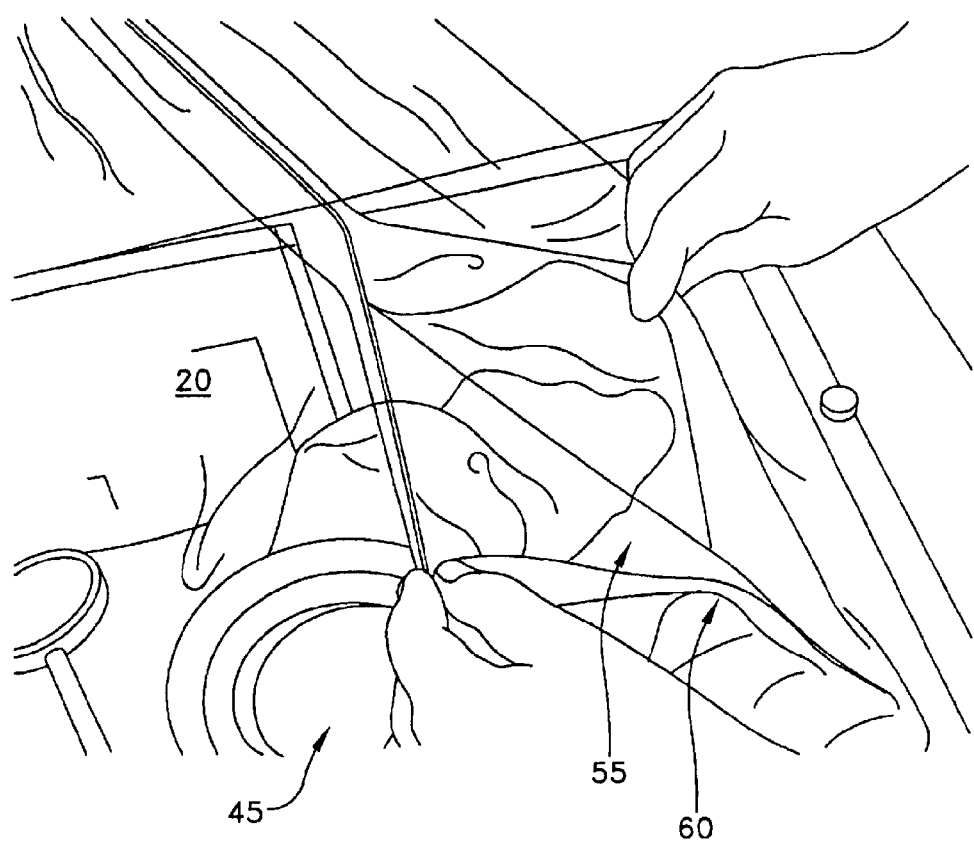
FIG. 4 is a schematic perspective view showing the sealable opening of the isolation glove box.
Figure 5:
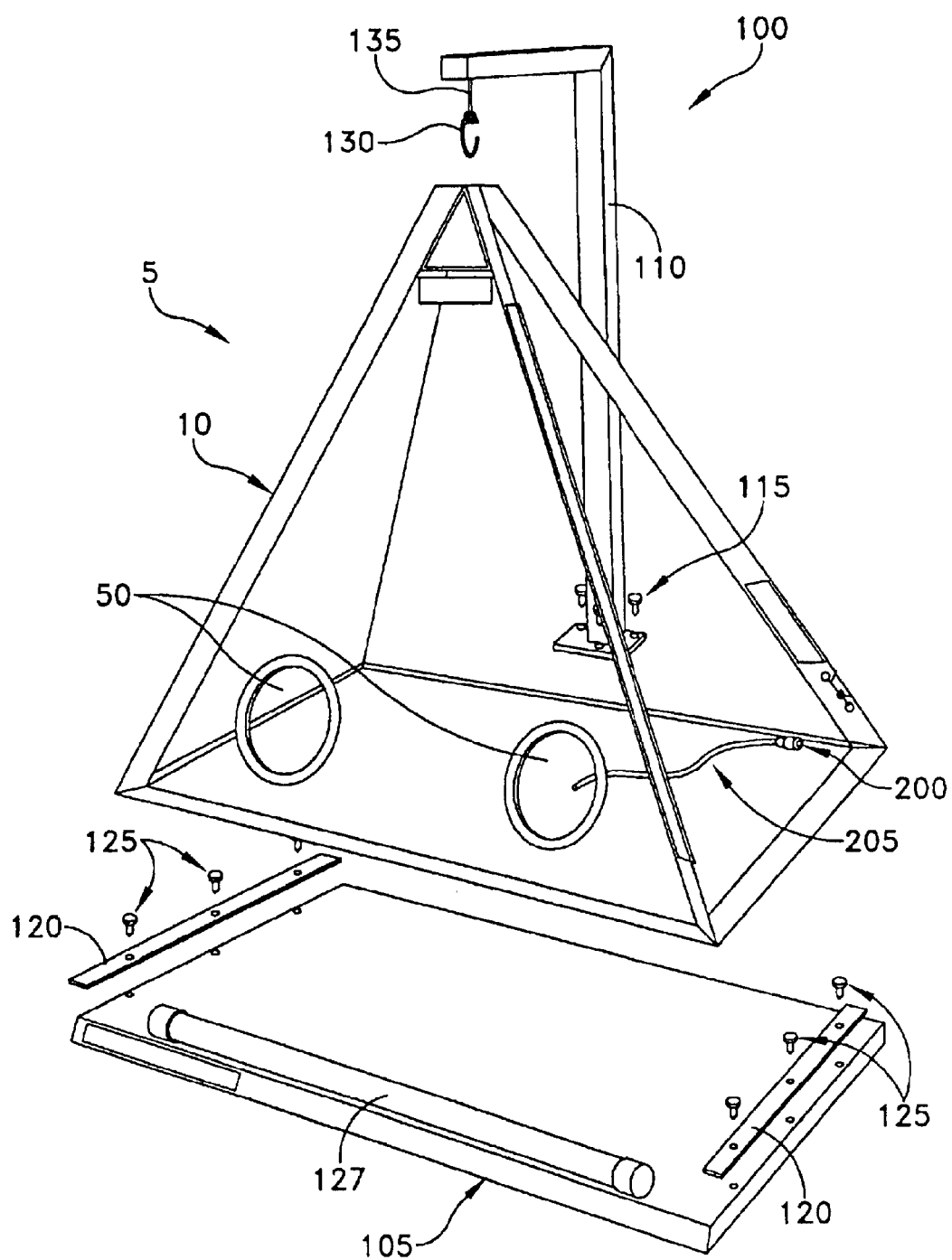
FIG. 5 is a schematic perspective view of the enclosure of the isolation glove box adjacent a support.
Figure 6:
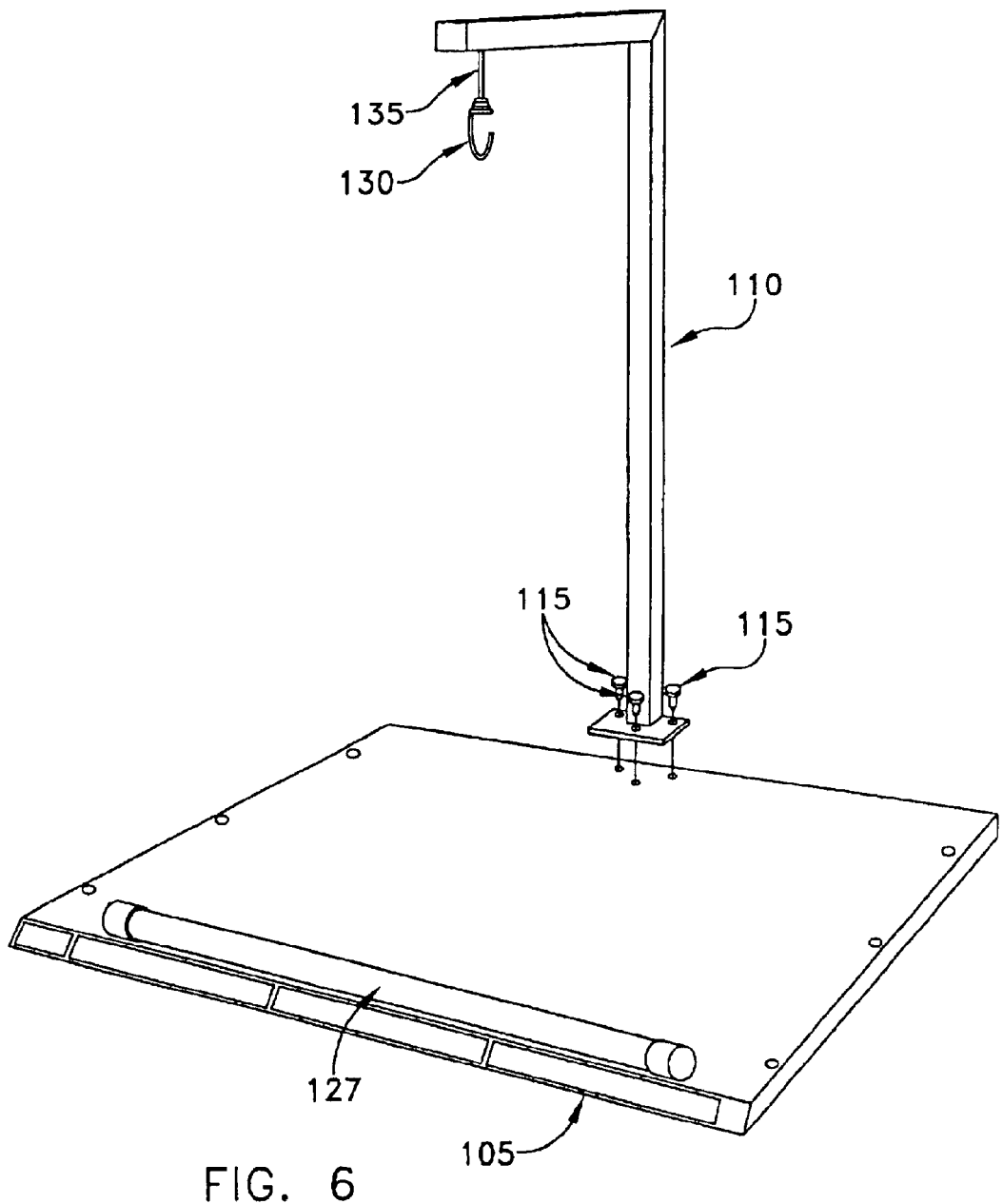
FIG. 6 is a schematic perspective view showing selected features of the support.
Figure 7:
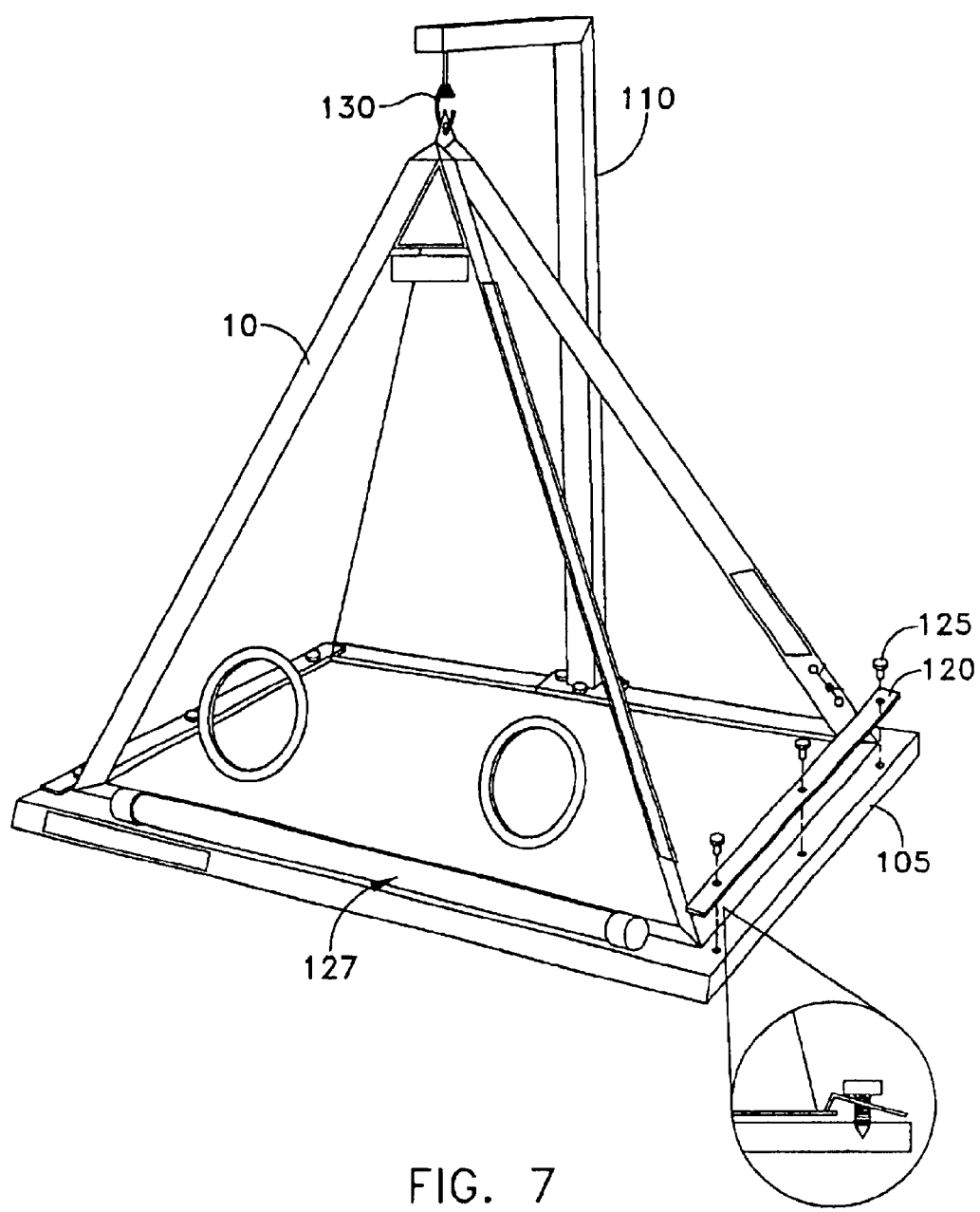
FIGS. 7 and 8 show the isolation glove box being attached to its support.
Figure 8:
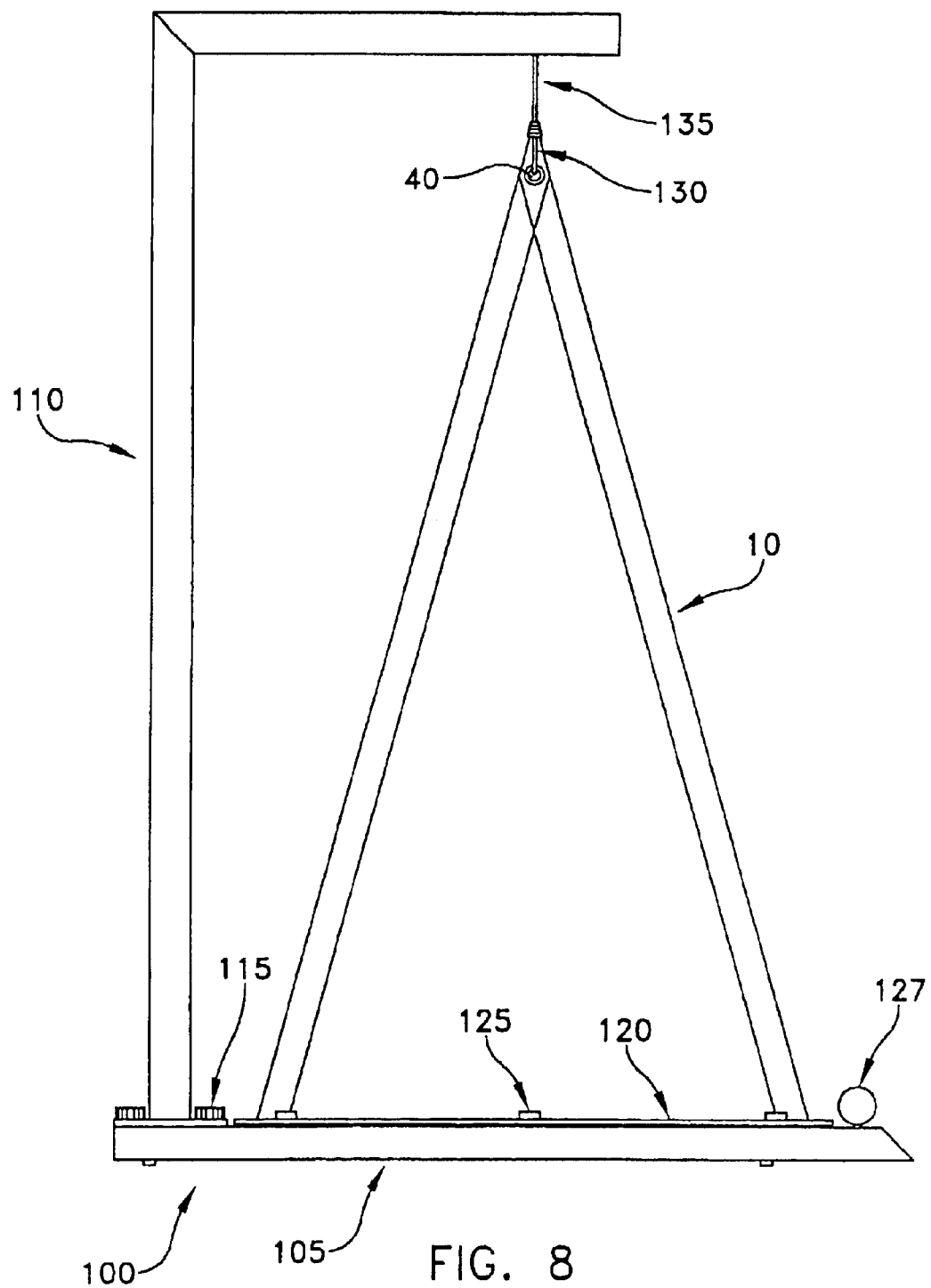

One or more sealable openings 55 are formed in enclosure 10. Sealable openings 55 may be formed on any of the edges 35 or sides 20 of the pyramidal enclosure 10. Each of the sealable openings 55 is provided with an airtight opening and closing mechanism 60, thus allowing for the introduction of specimens into the interior of enclosure 10 and the subsequent airtight sealing of the enclosure. By way of example, airtight opening and closing mechanism 60 may comprise a so-called "zip lock" seal such as that shown in FIG. 4.

Isolation glove box 5 preferably has a mat 65 within its interior, atop base 15, in order to protect the soft PVC of base 15 from damage when working on a specimen with sharp tools within the enclosure (e.g., such as when opening a suspicious package placed inside isolation glove box 5). In one preferred form of the invention, mat 65 is made of soft, very thick PVC. If desired, mat 65 may have an additional sheet of PVC placed on its top, whereby it will be sandwiched between two PVC sheets (i.e., the base sheet 15 and the additional sheet). Preferably mat 65 is opaque and provides a good contrast for objects placed inside enclosure 10.

By making isolation glove box 5 sufficiently inexpensive, and by forming it out of appropriate materials, the isolation glove box (with or without its contents) may be quickly and easily disposed of (e.g., by incineration or other appropriate technique) at the conclusion of an investigation.

As noted above, in one preferred form of the invention, inclined walls 20 have a configuration and sufficient inherent rigidity that enclosure 10, once erected, will stay erected. Preferably, however, isolation glove box 5 is used in conjunction with a support to (i) help keep enclosure 10 erect, and (ii) prevent the isolation glove box from sliding about a worksurface during use.

Accordingly, and looking now at FIGS. 5–8, in one preferred form of the invention, a support 100 is provided. Support 100 generally comprises a rigid base 105 and an upstanding arm 110 which is releasably attached (e.g., with screws 115) to base 105. Base 105 preferably has a pair of releasable runners 120 which can be used to releasably secure isolation glove box 5 to base 105. Releasable runners 120 are preferably releasably connected to base 105 by screws 125. A wrist support 127 may also be secured to base 105 if desired.

Upstanding arm 110 has, at its upper end, a hook 130. Preferably an elastic element 135 (e.g., a spring or a rubber strip) is interposed between upstanding arm 110 and hook 130, whereby to allow some stretching of the sides of enclosure 10 during use.

Isolation glove box 5 may be used as follows.

When an investigation is to be conducted (e.g., a relatively simple and inexpensive investigation in a laboratory, or a preliminary examination in the field, etc.), support 100 is set up (if it is not already set up) and isolation glove box 5 is erected and attached to the support. More particularly, (i) support 100 is set up by attaching upstanding arm 110 to rigid base 105, (ii) isolation glove box 5 is erected from its folded condition (FIG. 3) to its erect position (FIG. 2) by pulling its apex 25 upward relative to its base 15, (iii) base 15 of enclosure 10 is secured to rigid base 105 of support 100 by capturing base wings 35 beneath runners 120, and (iv) apex 25 of enclosure 10 is attached to hook 130 by lifting the apex upward and slipping eyelet 40 onto hook 130.

Next, the specimen is placed inside isolation glove box 5, i.e., by opening sealable opening 55 if it is not already open, placing the specimen (and anything else needed for the investigation, such as tools, etc.) inside the enclosure, and then closing sealable opening 55.

At this point the specimen may be investigated, safely in the case of potentially pathogenic substances and/or without contamination in the case of contaminable substances, using gloves 45.

Figure 9:
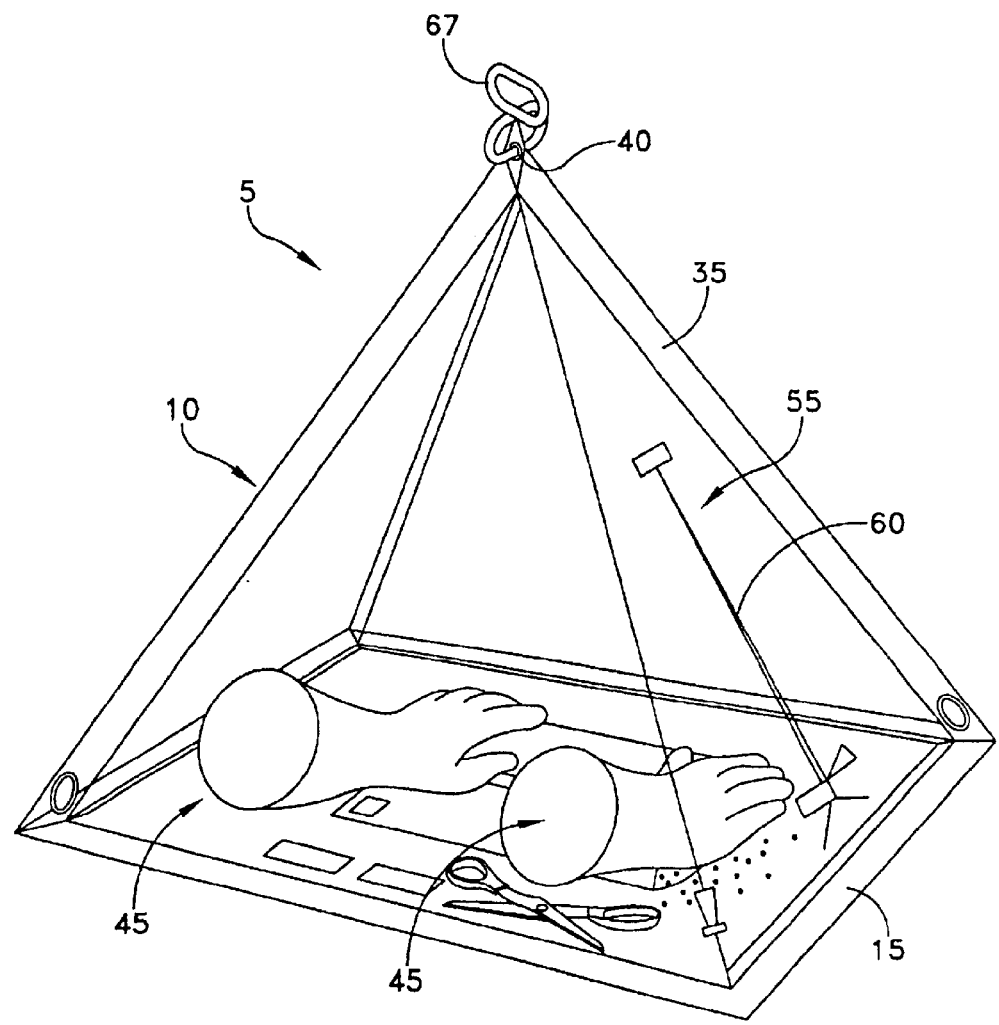
FIG. 9 shows the isolation glove box with a carrying handle attached thereto.

After the intended investigation, isolation glove box 5 (with or without specimen) may then be disposed of or, if desired, it may be transported (with specimen) to another location for further investigation.

Where isolation glove box 5 is to be disposed of, the isolation glove box is dismounted from support 100 and transported, e.g., without opening, to an appropriate disposal facility, e.g., an incinerator. In this respect it will be appreciated that by the proper selection of inexpensive and disposable construction materials, the entire isolation glove box may be disposed of as a unit, without requiring the release of the specimen contained in the isolation glove box.

Where isolation glove box 5 is to be transported to another location for further investigation (e.g., in the case of a suspicious mail package which may contain anthrax), the isolation glove box is dismounted from support 100 so that the suspicious contents may be transported, without danger, within the sealed enclosure to a specialized laboratory for a more thorough analysis. To this end, a carrying handle 67 (FIG. 9) may be inserted in top eyelet 40 so as to facilitate transport, including the possible suspension of the enclosure 10 inside a vehicle during transport.

A spare isolation glove box 5 (FIG. 2), previously folded (FIG. 3), may then be installed on a support 100 (FIG. 5) when needed for subsequent investigations.

It should be appreciated that the generally pyramidal shape of enclosure 10 is highly advantageous, inasmuch as the apex of the pyramid allows for a single point of attachment (e.g., for support 100 and/or handle 67), thereby eliminating any need for a complex structure in order to provide support for the enclosure during use and/or transport.

In one preferred form of the invention, isolation glove box 5 includes a port assembly 200 (FIGS. 1, 2 and 5) formed in one of the inclined walls 20 of enclosure 10. Port assembly 200 permits air to be evacuated from the interior of isolation glove box in a controlled fashion, e.g., for sampling, for biological culturing, etc. In this respect it will be appreciated that such air will carry with it some or all of the specimen placed inside enclosure 10, whereby to easily obtain the same. If desired, a tube 205 may be attached to the interior of port 200 to allow convenient suction pickup of specimen material.

Figure 10:
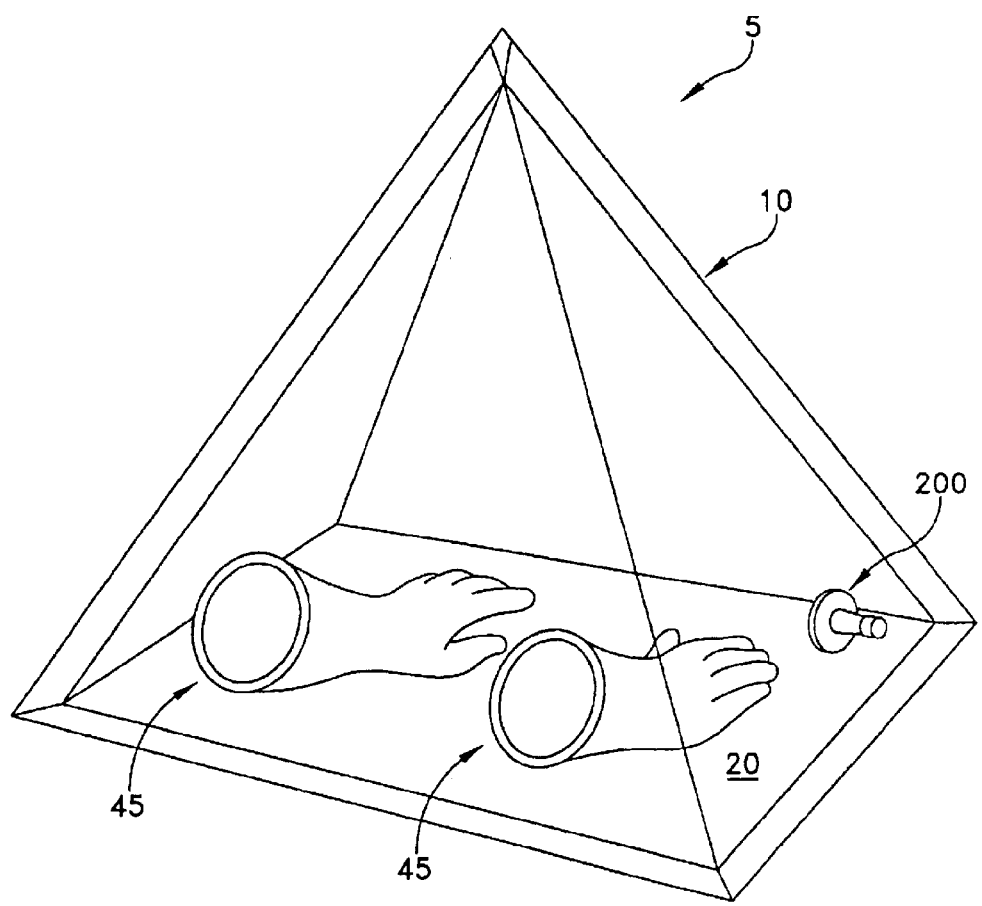
FIG. 10 is a schematic perspective view showing a port assembly in the wall of the isolation glove box.
Figure 11:
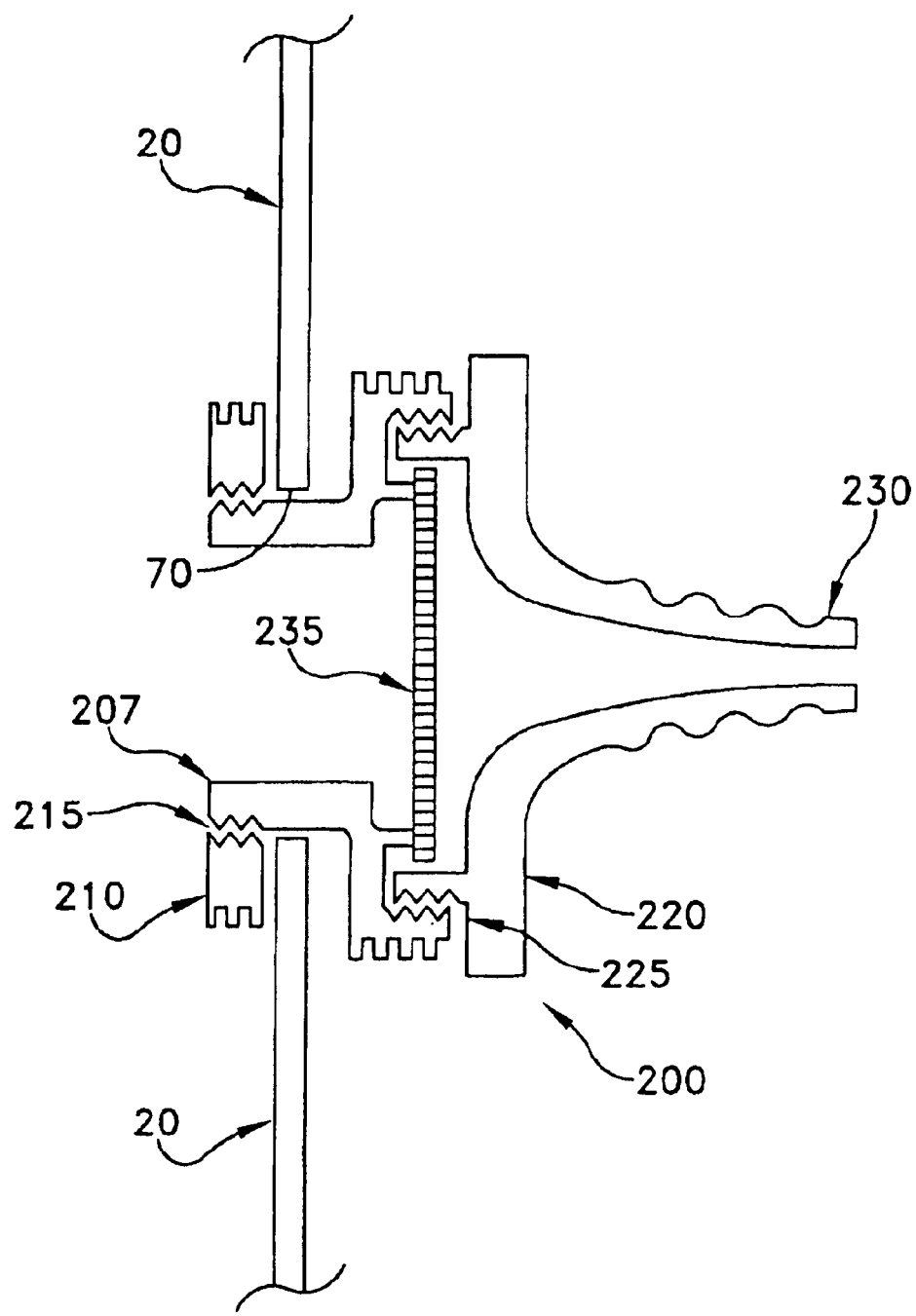
FIG. 11 shows further details of the port assembly shown in FIG. 10.
Figure 12:
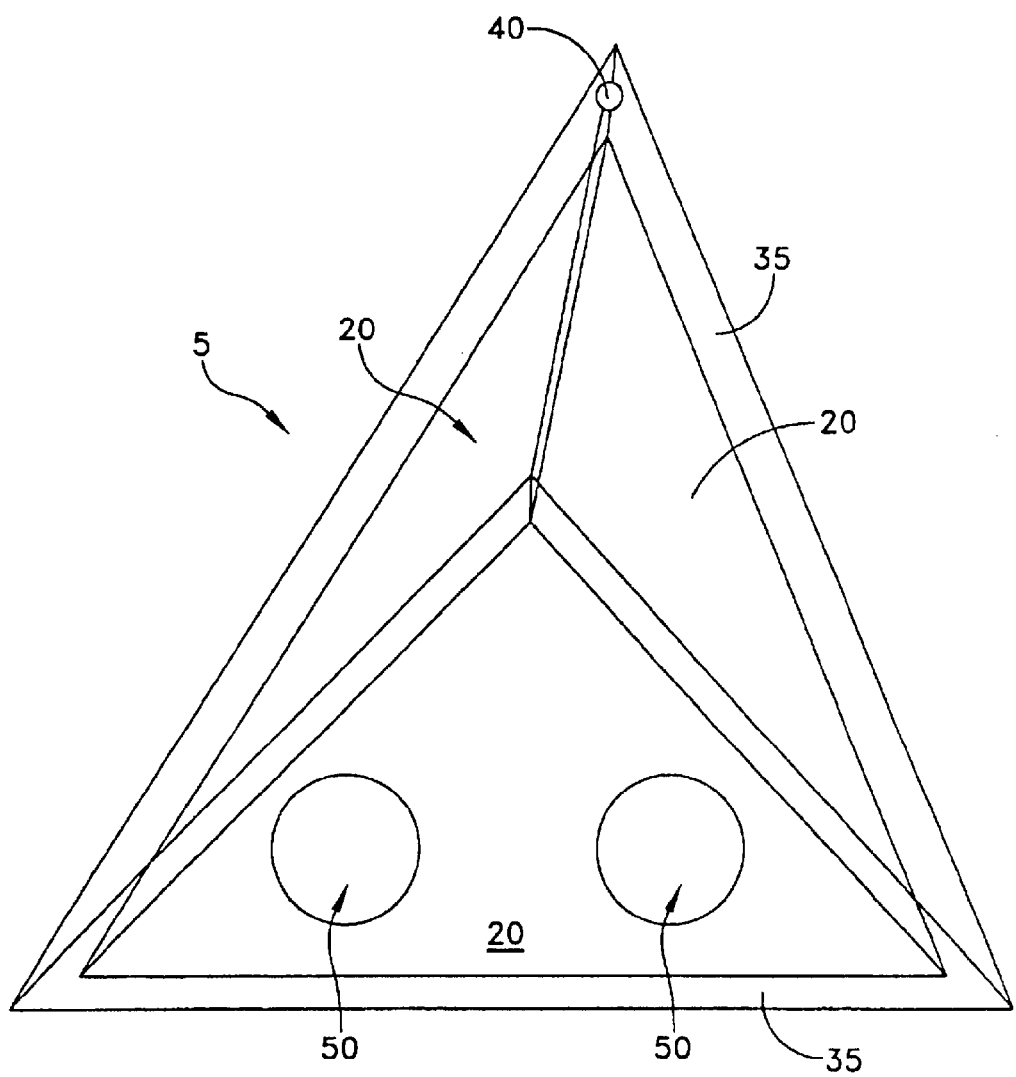
FIGS. 12–14 show alternative constructions for the enclosure of the isolation glove box.

In one preferred form of the invention, and looking now at FIGS. 10 and 11, port assembly 200 comprises a body 207 for attachment about the periphery of an opening 70 in an inclined wall 20 of enclosure 10. Body 207 may be secured to inclined wall 20 in a variety of ways, e.g., through the use of a locking ring 210 and screw threads 215. Port assembly 200 also comprises a fitting 220 that can be removably attached to body 207, e.g., with screw threads 225. Fitting 220 may be provided with a ribbed nipple 230 for connection to a hose linked to a vacuum pump, in order to withdraw air (and hence specimen material) from the interior of the enclosure. A cap (not shown) may be secured over nipple 230. A biological microporous filtration membrane 235 is releasably captured between body 207 and fitting 220.

On account of this construction, once the specimen has been placed inside enclosure 10 and, if necessary, isolation glove box 5 transported to an analysis facility, a vacuum line is connected to nipple 230 of fitting 220 and air is removed from the interior of enclosure 10. If desired, prior to or during this evacuation, the specimen may be stirred up or otherwise manipulated with the help of the integrated gloves 45. This operation, done entirely under negative pressure, is without danger for the user and the environment, and the user can perform it without the use of complex or heavy equipment. At this stage, the filtration membrane 235 can be safely removed from port assembly 200 and then analyzed, e.g., sampled and/or used to spark a growth that will then be ready for microscopic analysis. If the analysis is positive, the enclosure and its contents can then be safely delivered to another site if appropriate, e.g., to police investigation units in the case of an anthrax-bearing package.

It is also possible to provide a port assembly 200 which omits membrane 235. In this case, body 205 and fitting 220 may be formed with a singular construction, and the filtration membrane 235 may be provided anywhere between port assembly 200 and the vacuum source.

Port assembly 200 (and/or additional ports) can also be used to introduce gas into the enclosure 10. By way of example, port assembly 200 (or other ports) may be used to introduce an inert gas (e.g., nitrogen) into enclosure 10 so as to create an inert atmosphere within the enclosure. This may be easily accomplished by, for example, first attaching a vacuum pump to the port assembly so as to remove the air from within the enclosure, and then introducing an inert gas within the enclosure. In this respect it should be appreciated that removal of the air from within enclosure 10 will typically cause the enclosure to collapse flat, and introduction of the inert gas into the enclosure will cause the enclosure to regain its shape.

In one preferred form of the invention, the invention may be used to investigate suspicious (e.g., potentially anthrax-bearing) mail. In this form of the invention, there are four distinct phases of the use. At each stage, the user can benefit from specific features built into the invention so as to facilitate their work.

First is the opening of the suspicious mail. There, the invention's simple and flexible design enables a first user to set up the isolation glove box and use it quickly and easily with little or no training, unlike a traditional glove box or complex biosafety cabinet.

Second is the transport of the suspicious mail. Once the first user discovers a suspicious substance inside the mail, the proper authorities or second user transports the detachable flexible enclosure, using the built-in eyelet, to a laboratory for analysis.

Third is the analysis of the specimen found inside the contents of the mail. The third user, a trained lab technician, connects the enclosure up to a vacuum pump with the help of the built-in port so as to extract the powders and concentrate them on a filter membrane for proper and accurate analysis.

Fourth is the inspection of the evidence for criminal investigation purposes. Once the analytical lab has performed its testing on the powder, the enclosure and its preserved, untainted contents can be picked up by its fourth user, e.g., an FBI crime lab, who can test the envelope or package for fingerprints or handwriting analysis in order to learn the identity of its sender.

During each of the phases, all users along the way have been protected and the integrity of the evidence inside the enclosure has been preserved, undamaged and untainted.

It should, of course, be appreciated that various modifications may be made to the preferred embodiments described above without departing from the scope of the present invention.

Figure 13:
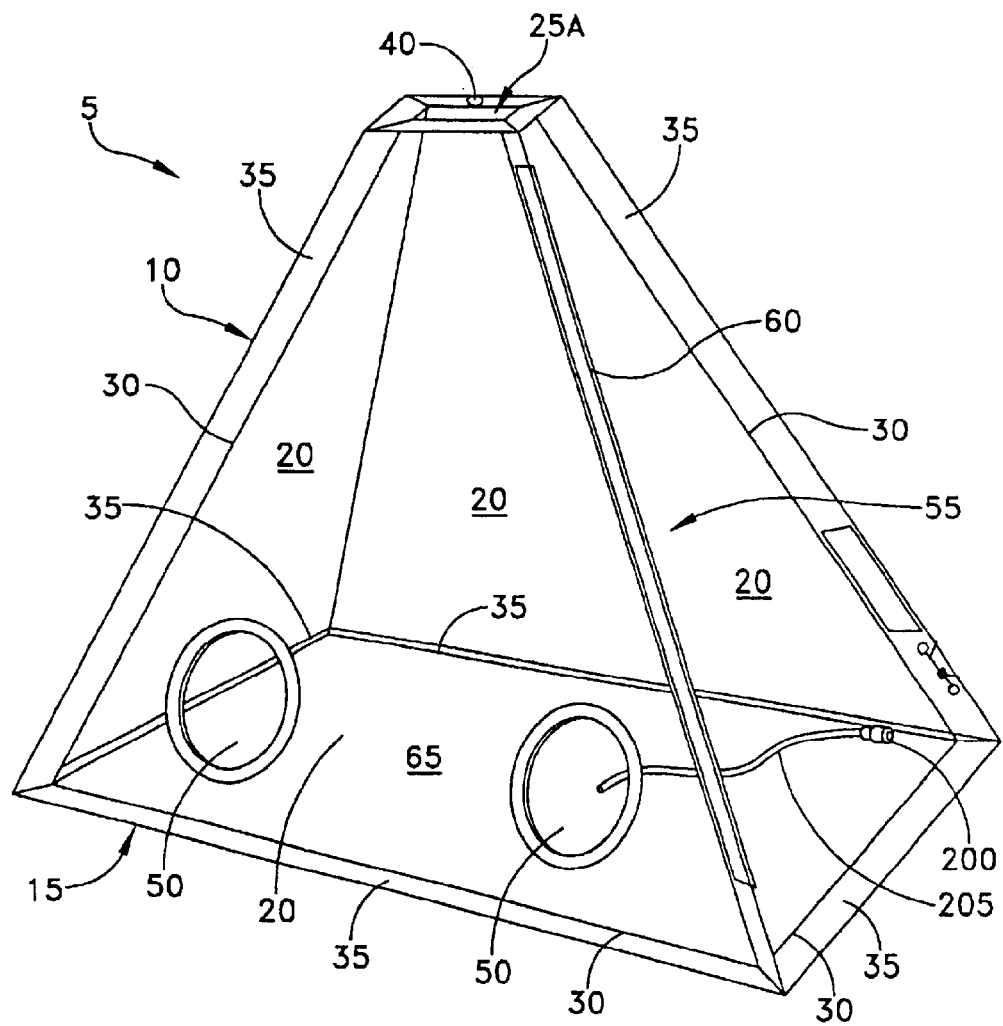
Figure 14:
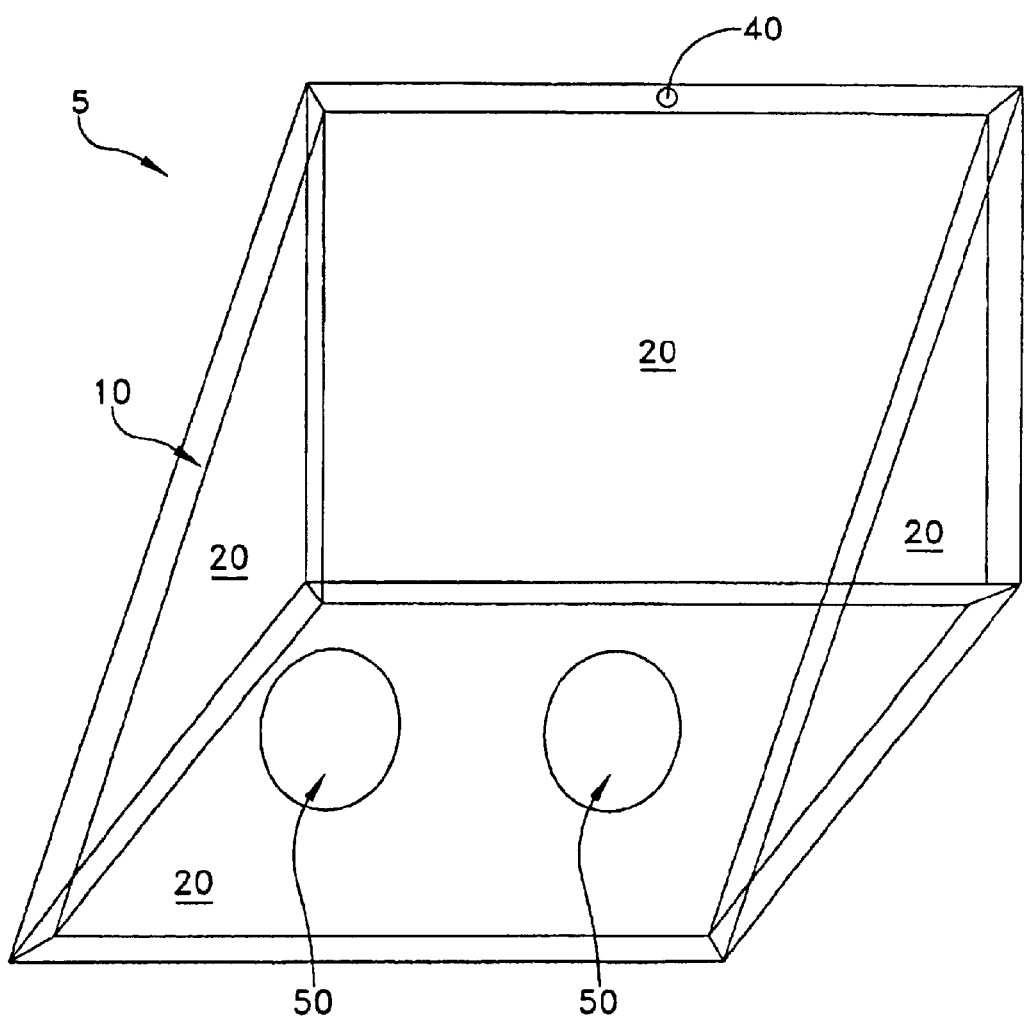

Thus, for example, in the preferred embodiments enclosure 10 is in the form of a pyramid comprising a base 15 having four sides (e.g., rectangular or square) and four inclined walls 20 intersecting at an apex 25 (FIGS. 1 and 2). However, isolation glove box 5 may also have a three-sided base 15 and three inclined walls 20 (FIG. 11), or it may have a five-sided base 15 and five inclined walls 20, etc.; and/or isolation glove box 5 could be formed so that its inclined walls 20 terminate short of intersecting, e.g., each inclined wall 20 could have a trapezoidal shape (FIG. 13), with a top 25A extending between the upper ends of inclined walls 20; and/or isolation glove box 5 could have one inclined wall 20 (i.e., the "front" wall), with the remainder of the walls being substantially vertical (FIG. 14).

Furthermore, in the preferred embodiments, support 100 comprises a single upstanding arm 110 which interposes an elastic element 135 between the arm and hook 130. However, if desired, upstanding arm 110 could also be formed so as to have some elasticity, i.e., so that elastic element 135 could be assisted by, or even entirely replaced by, the elasticity of the upstanding arm 110 if desired.

Figure 15:
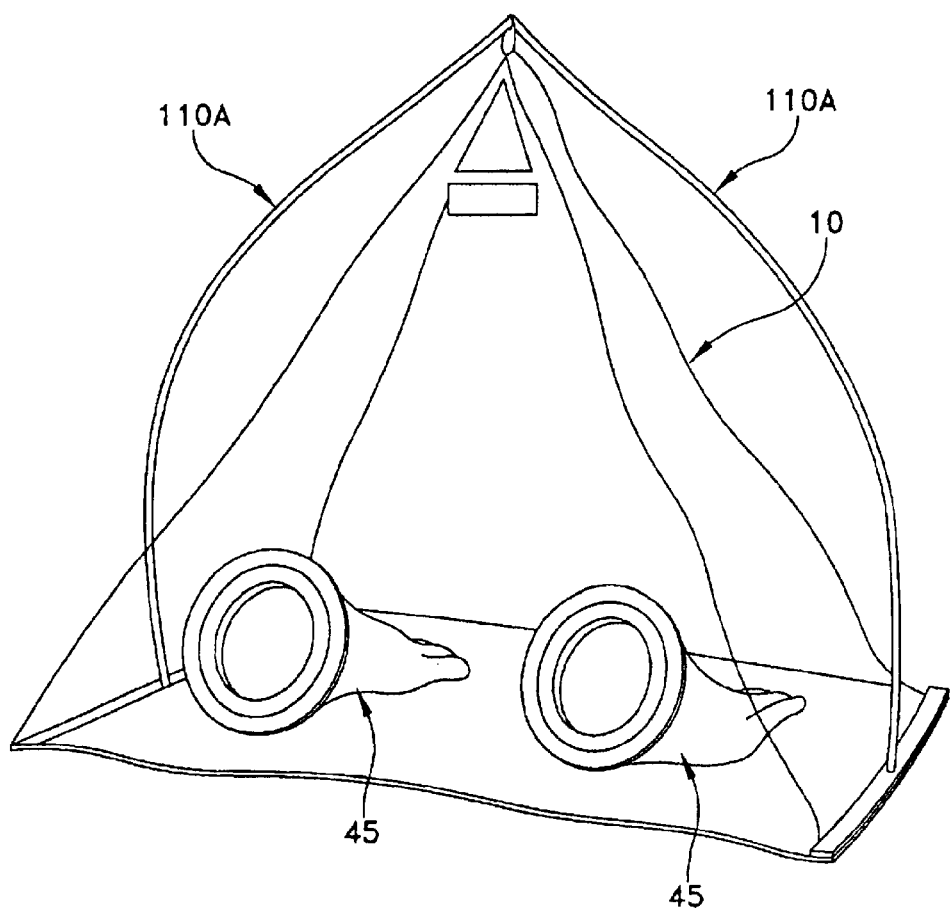
FIG. 15 shows an alternative construction for the support.

Furthermore, if desired, the single upstanding arm 110 may be replaced by two or more hoop arms 110A (FIG. 15).

These and other changes of their type are considered to be within the scope of the present invention.

What is claimed is:

1. A mobile, disposable isolation glove box comprising:
   an enclosure comprising a base and a plurality of inclined walls converging to an apex, at least one of said walls being at least in part transparent;
   at least one glove formed in at least one of said inclined walls, said at least one glove extending into the interior of said enclosure; and
   a sealable opening formed in said enclosure for permitting a specimen to be placed inside said enclosure;
   wherein said enclosure is formed by welding or glueing said base and said plurality of inclined walls to one another; and
   wherein said welding or glueing is along a substantially straight line inboard from a periphery of said base and said plurality of inclined walls, whereby to form wings at edges of said enclosure.

2. A mobile, disposable isolation glove box according to claim 1 wherein said enclosure is pathogen impervious.

3. A mobile, disposable isolation glove box according to claim 1 wherein said enclosure is contaminant impervious.

4. A mobile, disposable isolation glove box according to claim 1 wherein said enclosure is formed so as to be (i) substantially self-standing, and (ii) capable of being folded substantially flat.

5. A mobile, disposable isolation glove box according to claim 1 wherein said enclosure comprises a loop for connecting said isolation glove box to another element.

6. A mobile, disposable isolation glove box according to claim 5 wherein said loop comprises an eyelet formed in said enclosure.

7. A mobile, disposable isolation glove box according to claim 5 wherein said loop comprises a ring passed through a portion of said enclosure.

8. A mobile, disposable isolation glove box according to claim 1 wherein the apex comprises a point.

9. A mobile, disposable isolation glove box according to claim 1 wherein the apex comprises a relatively small, substantially flat surface.

10. A mobile, disposable isolation glove box according to claim 1 wherein said enclosure comprises four of said inclined walls.

11. A mobile, disposable isolation glove box according to claim 10 wherein said enclosure base is provided with four sides and said four inclined walls terminate in an apex.

12. A mobile, disposable isolation glove box according to claim 1 wherein said enclosure comprises three of said inclined walls.

13. A mobile, disposable isolation glove box according to claim 1 wherein said plurality of inclined walls are transparent.

14. A mobile, disposable isolation glove box according to claim 1 wherein said plurality of inclined walls are formed out of polyvinylchloride.

15. A mobile, disposable isolation glove box according to claim 1 wherein said base is formed out of polyvinylchloride.

16. A mobile, disposable isolation glove box according to claim 1 wherein an eyelet is formed in one of said wings.

17. A mobile, disposable isolation glove box according to claim 1 wherein said at least one glove comprises two gloves.

18. A mobile, disposable isolation glove box according to claim 17 wherein said two gloves are formed in the same inclined wall.

19. A mobile, disposable isolation glove box according to claim 1 wherein said sealable opening comprises a zip-lock seal.

20. A mobile, disposable isolation glove box according to claim 1 further comprising a port formed in one of said inclined walls.

21. A mobile, disposable isolation glove box according to claim 20 wherein said port comprises a filter membrane.

22. A mobile, disposable isolation glove box according to claim 21 wherein said filter membrane is disposed between the interior of said enclosure and a vacuum source.

23. A mobile, disposable isolation glove box according to claim 20 wherein said port may be selectively connected to (i) a vacuum source, and (ii) a source of inert gas, whereby air within said enclosure may be replaced by inert gas.

24. A mobile, disposable isolation glove box assembly comprising:
   a mobile, disposable isolation glove box comprising:
   an enclosure comprising a base and a plurality of inclined walls converging to an apex, at least one of said walls being at least in part transparent;
   at least one glove formed in at least one of said inclined walls, said at least one glove extending into an interior of said enclosure; and
   a sealable opening formed in said enclosure for permitting a specimen to be placed inside said enclosure; and a support for supporting said isolation glove box on a worksurface, said support comprising at least one upstanding element extending above the height of the apex and including apparatus for connection to the apex, whereby to support said enclosure in an upright position; and wherein said at least one upstanding element comprises a hoop formed by at least two hoop arms.

25. An assembly according to claim 24 wherein said support further comprises a substantially rigid base connected to said upstanding element.

26. An assembly according to claim 25 wherein said substantially rigid base is sized to accommodate said enclosure base thereon.

27. An assembly according to claim 26 wherein said support base includes means for releasably securing said enclosure base to said support base.

28. An assembly according to claim 24 wherein said at least one upstanding element comprises an L-shaped bracket.

29. A method for conducting an investigation of a potentially pathogenic or contaminable specimen, wherein the specimen is located at a first location, said method comprising the steps of:

providing a mobile, disposable isolation glove box comprising:

an enclosure comprising a base and a plurality of inclined walls converging to an apex, at least one of said walls being at least in part transparent;

wherein said enclosure is formed by welding or glueing said base and said plurality of inclined walls to one another; and wherein the welding or glueing is along a substantially straight line inboard of a periphery of said base and said plurality of inclined walls, whereby to form wings at the edges of said enclosure;

at least one glove formed in at least one of said inclined walls, said at least one glove extending into the interior of said enclosure; and a sealable opening formed in said enclosure for permitting a specimen to be placed inside said enclosure;

placing the specimen inside said enclosure and closing said sealable opening;

conducting a preliminary examination using said isolation glove box at said first location;

transporting said isolation glove box, with the specimen sealed therein, to a second location; and conducting a follow-up examination using said isolation glove box at the second location.

30. A method according to claim 29 wherein said method further comprises the step of disposing of said isolation glove box with said specimen therein.

* * * * *